(12) United States Patent
Wang et al.

(10) Patent No.: US 11,014,974 B2
(45) Date of Patent: May 25, 2021

(54) NON-ANTIBODY BINDING PROTEINS BINDING TO PD-1 RECEPTORS AND USES THEREOF

(71) Applicants: Oral Subsidiary Sun Yat-sen University Hospital, Guangzhou (CN); Guangzhou Yidai Pharmaceutical Co., Ltd., Guangzhou (CN)

(72) Inventors: Hua Wang, Guangzhou (CN); Xiaofeng Huang, Guangzhou (CN); Long Zhao, Guangzhou (CN); Yan Zhang, Guangzhou (CN)

(73) Assignees: ORAL SUBSIDIARY SUN YAT-SEN UNIVERSITY HOSPITAL, Guangzhou (CN); GUANGZHOU YIDAI PHARMACEUTICAL CO., LTD., Guangzhou (CN)

( * ) Notice: Subject to any disclaimer, the term of this patent is extended or adjusted under 35 U.S.C. 154(b) by 0 days.

(21) Appl. No.: 16/612,455

(22) PCT Filed: Sep. 6, 2017

(86) PCT No.: PCT/CN2017/100717
§ 371 (c)(1),
(2) Date: Nov. 11, 2019

(87) PCT Pub. No.: WO2018/205472
PCT Pub. Date: Nov. 15, 2018

(65) Prior Publication Data
US 2020/0095304 A1 Mar. 26, 2020

(30) Foreign Application Priority Data
May 9, 2017 (CN) .......................... 201710324664.7

(51) Int. Cl.
*A61K 38/00* (2006.01)
*A61P 35/00* (2006.01)
*C07K 14/705* (2006.01)
*C12N 5/0783* (2010.01)
*C12N 15/86* (2006.01)

(52) U.S. Cl.
CPC ........ *C07K 14/70521* (2013.01); *A61P 35/00* (2018.01); *C12N 5/0636* (2013.01); *C12N 15/86* (2013.01); *A61K 38/00* (2013.01); *C12N 2740/15043* (2013.01)

(58) Field of Classification Search
None
See application file for complete search history.

(56) References Cited

U.S. PATENT DOCUMENTS

2016/0017011 A1  1/2016  Wang

FOREIGN PATENT DOCUMENTS

| CN | 103897036 A | 7/2014 |
| CN | 103936836 A | 7/2014 |
| CN | 104761633 A | 7/2015 |
| CN | 103897036 B | 2/2016 |
| CN | 103936836 B | 3/2016 |
| WO | 2014/134084 A2 | 9/2014 |

OTHER PUBLICATIONS

Li et al. (Oncotarget. Oct. 4, 2016;7(40):64967-64976) (Year: 2016).*
Li, Qiao et al. Discovery of peptide inhibitors targeting human programmed death 1 (PD-1) receptor; Oncotarget, vol. 7, No. 40.
International Search Report for PCT/CN2017/100717, dated Feb. 9, 2018.

* cited by examiner

*Primary Examiner* — Sergio Coffa
(74) *Attorney, Agent, or Firm* — Schmeiser, Olsen & Watts, LLP

(57) ABSTRACT

Provided is a non-antibody binding protein binding to PD-1 receptor which has a sequence as shown in SEQ ID NO:1 and its analogues. Also provided is use of the non-antibody binding protein in the preparation of a formulation for treating PD-1 pathway related diseases.

2 Claims, 8 Drawing Sheets

Specification includes a Sequence Listing.

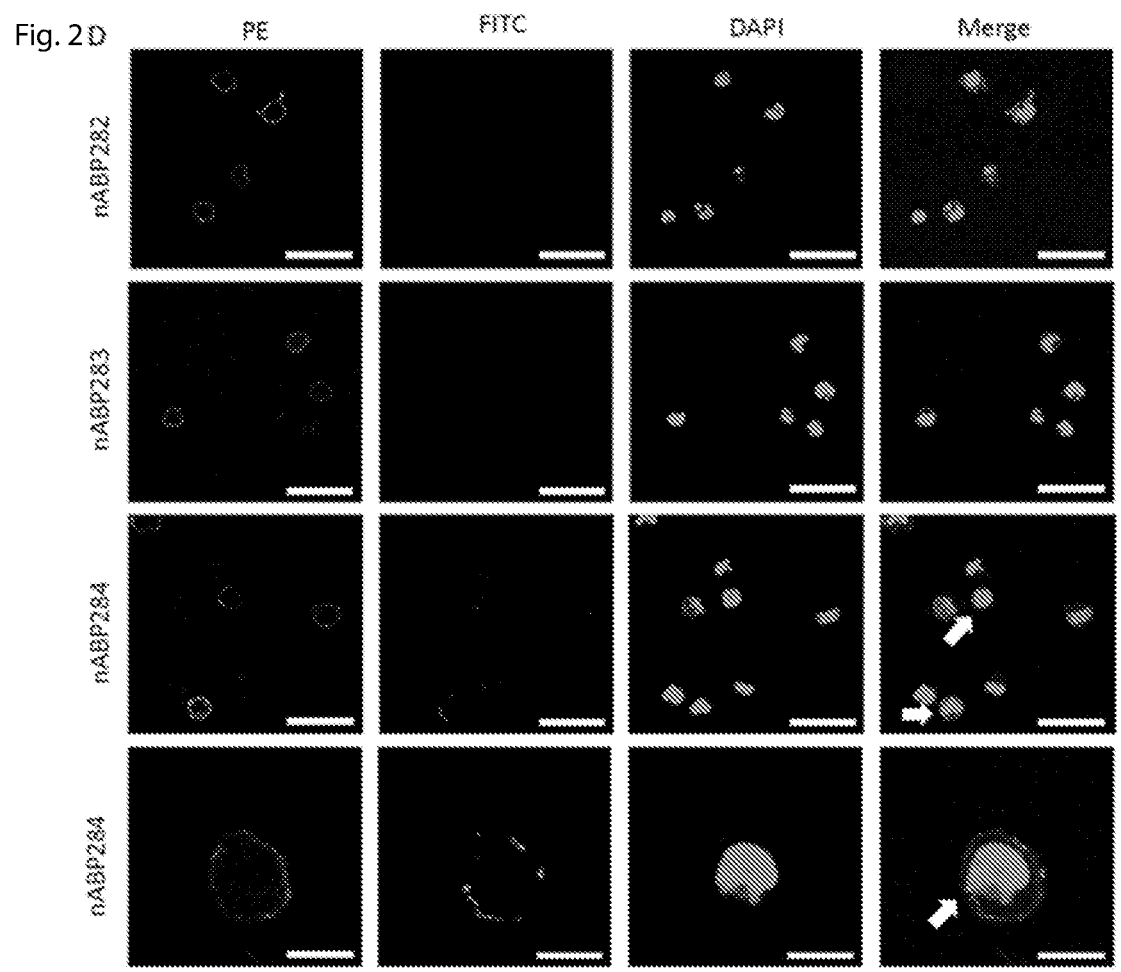

NON-ANTIBODY BINDING PROTEINS BINDING TO PD-1 RECEPTORS AND USES THEREOF

CROSS-REFERENCE TO RELATED APPLICATIONS

This application claims priority to PCT Application No. PCT/CN2017/100717, having a filing date of Sep. 6, 2017, which is based on Chinese Application No. 201710324664.7, having a filing date of May 9, 2017, the entire contents both of which are hereby incorporated by reference.

SEQUENCE LISTING

This application includes a separate sequence listing in compliance with the requirements of 37 C.F.R. §§ 1.824(a)(2)-1.824(a)(6) and 1.824(b), submitted under the file name "0081US01SEQUENCELISTINGASFILED", created on Apr. Nov. 8, 2019, having a file size of 2 KB, the contents of which are hereby incorporated by reference.

FIELD OF TECHNOLOGY

The following relates to the technical field of medical biotechnology, particularly, it relates to a non-antibody binding protein binding to PD-1 receptor and use thereof.

BACKGROUND

PD-1 (programmed cell death receptor1) is a transmembrane glycoprotein 1 consisted of 288 amino acids and is encoded by PDCD1 gene, and PD-1 has approximately 30% homologous sequence with CD28 and CTLA-4 (cytotoxic T lymphocyte related antigen 4). A structure of PD-1 comprises an immunoglobulin variable region (IgV)-like domain in an extracellular domain, a hydrophobic transmembrane region and an intracellular domain, wherein the intracellular domain includes an immunoreceptor tyrosine-based inhibitory motif (ITIM) and an immunoreceptor tyrosine-based switch motif (ITSM), and they both play an important role in PD-1 inhibitory signal pathway.

PD-1 expresses in activated T cells, B cells and NK cells, and participates in inhibition of persistent immune responses in peripheral organ and plays a significant role in preventing autoimmune injury. However, persistent activation of PD-1 may affect activation and proliferation of T cells to inhibit secretion of cytokines such as interleukin 2 (IL-2), and cause a T cells exhaustion, such that the tumor killing capacity of T cells is weakened.

The activation of PD-1 depends on binding to a ligand, PD-L1 or PD-L2. After PD-1 binds to the ligand, the downstream signal pathway is activated to inhibit function of T cells. PD-L1 and PD-L2 highly express in several types of tumor cells, such as melanoma, non-small cell lung cancer, breast carcinoma and soft tissue sarcoma, etc. Immune system of tumor patients is inhibited, because the expression of PD-L1 and PD-L2 in tumor cells are up-regulated, and they interact with PD-1 on the surface of T cells, leading to the T cells exhaustion, thus the tumor cells can evade attack of T cell.

Monoclonal antibody for PD-1 may block the interaction of PD-1/PD-L1, so that the function of T cells can be recovered to relieve the immune inhibition for tumor patients, thereby multiple tumors such as melanoma, non-small cell lung cancer can be well treated. It has been demonstrated by a number of clinical trials that a PD-1 therapeutic monoclonal antibody has a good therapeutic effect on treating melanoma, non-small cell lung cancer, and the immune suppression of the tumor patients is improved.

Increasing expression of PD-L1 in tumor cells for patient with head and neck squamous cell carcinoma (HNSCC) suggests that the immune state is similar to the immune state of melanoma patients, that is, in an immune suppression state. In peripheral blood of HNSCC patient, the proportions of $CD3^+$, $CD4^+$ and $CD8^+$ T cells are very low and this state remains even several years after the surgical treatments. In peripheral blood of the patient with HNSCC recurrence, the proportion of $CD4^+$ T cells is also very low, showing that the immune system is suppressed. The recognition and killing ability of cytotoxic T cell to HNSCC can be enhanced by a co-incubation between IFN-γ or exogenous tumor antigen and HNSCC cells, indicating that the immune treatment is able to enhance the recognition and killing ability of immune cells to tumor cells, thereby achieving a therapeutic effect on tumors. For those HNSCC patients treated with cellular immunotherapy after surgery and chemotherapy, their overall survival rate is obviously improved. PD-1 therapeutic monoclonal antibody, Pembrolizumab, shows a good efficacy in clinical trials of patients with recurrent HNSCC with PD-L1 positive expression. In one of phase I clinical trial where 173 HNSCC patients were recruited, overall objective response rate was 23.7%. In another clinical trial, (60) HNSCC patients were treated with Pembrolizumab, the overall objective response rate is 18% and the side effect is low. The above cellular immunotherapy and clinical trials of PD-1 monoclonal antibody treatment show that the immunotherapy is effective to HNSCC patients.

In an adoptive cell transfer (ACT), tumor-infiltrating lymphocytes or peripheral blood lymphocytes of patients are stimulated and proliferated in vitro through culturing, and then given back to the patients. It significantly enhances the efficacy to melanoma, malignant lymphoma, renal carcinoma, non-small cell lung cancer and HNSCC, and prolongs survival time of patient.

However, as tumor immune escape of patients continually exists, the tumor is still prone to recur and metastasize, and the long-term efficacy needs to be further improved. There are also some problems in the treatment of monoclonal antibody in cancer patients. First, PD-1 monoclonal antibody is a mouse original antibody, which inevitably causes human anti-mouse antibody immune response in human body, causing potential medical safety risks. Second, the molecular weight of PD-1 monoclonal antibody is relatively large, and the permeability to solid tumor tissue is weak, which affects the therapeutic effect on solid tumor. Third, the production cost of PD-1 monoclonal antibody is high, but the success rate is low, and the production cycle is long. These shortcomings also limit the use of PD-1 antibodies.

SUMMARY

An aspect relates to a non-antibody binding protein (nABP) binding to a PD-1 receptor and use thereof. The nABP has small molecular weight and high safety, and can be synthesized artificially.

It is a first aspect of the present disclosure to provide a non-antibody binding protein (nABP). The nABP has a sequence as shown in SEQ ID NO: 1 or similar to SEQ ID NO: 1, and it is named as PD-1-nABP284 (or nABP284).

The present disclosure further provides a use of the non-antibody binding protein as described hereinbefore, a use of the non-antibody binding protein in blocking PD-1 pathway, or a use of the non-antibody binding protein in the preparation of a PD-1 pathway blocker.

The non-antibody binding protein can also be used in the preparation of a regulator for enhancing a signal of the PD-1 pathway.

The non-antibody binding protein can also be used in the preparation of an immunomodulating drug and/or an anti-tumor drug.

Further, the non-antibody binding protein is also used in the preparation of an immunomodulating drug for treating diseases in relation to increasing secretion of PL-L1 and/or PD-L2 in vivo; or the non-antibody binding protein is also used in the preparation of a formulation for enhancing tumor-killing effects of immune cells which are cultured in vitro.

Further, the tumor is a tumor in tumor cells where the expression of PD-L1 and/or PD-L2 is up-regulated, such as but not limited to, melanoma, non-small cell lung cancer, breast carcinoma, soft tissue sarcoma. HNSCC, leukemia and malignant lymphoma.

The non-antibody binding protein can be used both in the preparation of a formulation for binding to PD-1 molecule or PD-1 positive cells and the preparation of an identifying reagent for binding to PD-1 molecule or PD-1 positive-cells.

Further, the PD-1 molecule is derived from total cellular proteins, cellular secretory proteins or the surface of living cells.

In one of specific embodiments, the PD-1 positive cells comprise leukemia cells, PD-1 positive lymphocytes in lymph node tissue, T cells, and NK cells.

The present further disclosure provides a formulation comprising the non-antibody binding protein described hereinbefore, and the formulation may be a pharmaceutical medicament or a cell identifying reagent. Further, the formulation may also comprise a pharmaceutically acceptable excipient or carrier, or an excipient or a carrier acceptable in molecular identity.

The non-antibody binding protein PD-1-nABP provided in the present disclosure is screened out by T7 phage library and PD-1 recombinant proteins.

The in vitro experiment proves that PD-1-nABP284 can not only bind to PD-1 proteins of total cellular proteins, but also bind to PD-1 proteins on the surface of living cells. Moreover, it can bind to PD-1 positive-lymphocytes in blood and lymph node tissue.

It is further proved by a research that the screened PD-1-nABP284 has no impact on proliferation of cell strains expressing PD-1 stably, and has no toxic effect on cell strains. Moreover, it also has no toxic effect in mice, with good safety and application prospect.

It is found by a research that PD-1-nABP284 is gathered in lymph nodes of groin and armpit in mice and the content of T lymphocytes is higher in the lymph nodes, which implies that PD-1-nABP284 tends to bind to PD-1 positive T lymphocytes in vivo, blocking the pathway for a binding between PD-1 and ligands such as PD-L1, and playing a role similar to PD-1 monoclonal antibody.

It is found by a research that PD-1-nABP284 and PD-L1 ligand competitively bind to PD-1 receptor on the surface of Jurkat tumor cell strains, and the PD-1-nABP284 plays a competitive binding role similar to PD-1 targeting monoclonal antibody drugs.

It is found by a research that when PD-1-nABP284 binds to PD-1 receptor, the suppression of PD-L ligand on secretion of interleukin-2 can be reversed, implying that the PD-1-nABP284 plays a humoral immunomodulation role similar to PD-1 targeting monoclonal antibody drugs.

It is found by a research that adding PD-1-nABP284 into a culture solution for co-culturing the lymphocyte and CAL 27 tongue cancer cell strain enhances the killing effect of the lymphocyte on the cancer cell, which is similar to the anti-tumor effect of PD-1 targeting monoclonal antibody drugs.

Compared to the therapeutic antibody, the non-antibody binding protein (also called as peptide) of the present disclosure is artificially synthesized and has low immunogenicity, high stability in vivo, great tumor penetrability, enhanced tumor accumulation and low manufacturing costs.

It is found by a research that PD-1-nABP284 binds to Jurkat tumor cell strains, which implies that PD-1-nABP284 is likely to tend to bind to PD-1 positive tumor cells, blocking the PD-1/PD-L1 pathway, and it plays a role similar to PD-1 monoclonal antibody.

The non-antibody binding protein of the present disclosure has a variety of advantages. Firstly, the non-antibody binding protein has a small molecular weight and great penetrability. Secondly, it can be artificially synthesized with low cost, and it is safe due to animal origin free. The non-antibody binding protein is capable of binding to certain molecules well, and plays a role similar to or even better than monoclonal antibody.

BRIEF DESCRIPTION

Some of the embodiments will be described in detail, with reference to the following figures, wherein like designations denote like members, wherein:

FIG. 2D shows testing results of immunofluorescence assay of affinity of nABP284, nABP283, nABP282 to PD-1 on the surface of OE-Jurkat cells;

DETAILED DESCRIPTION

Figure 1:
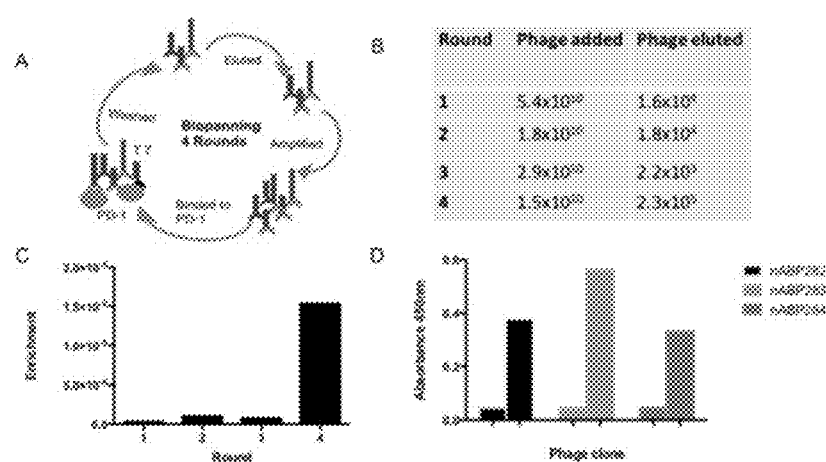
FIG. 1A depicts a schematic view of screening T7 phage library.
FIG. 1B depicts results after 4-rounds screenings of phage.
FIG. 1C depicts a recovery rate of each round.
FIG. 1D depicts absorbance values of three screened DNA sequences detected by ELISA.

The technical solution of the present disclosure will be further explained hereinafter with reference to the accompanying figures and detailed examples embodiments.

Main research method used in the examples comprises screening of T7 phage library, construction of PD-1 over expressed lentiviral vector, transfection and screening of PD-1 over expressed cell strains, immunoprecipitation assay, confocal microscope observation for immunofluorescence assay of co-labeling non-antibody binding protein and antibody, flow cytometry, cell proliferation assay, cytotoxicity assay, living mouse imaging, western blot and so on. Unless otherwise specified, the experimental operations are routine experimental operations learned by the skilled person in the art. The reagents used are commercially available if no otherwise specified.

Some reagents used in the examples are illustrated as follows:

Human PD-1 recombinant protein (PD1-HC214, Acrobiosystem), T7 phage library (D00154997, Novagen), Human PD-L1-Fc recombinant protein (10084-H02H-100, Sino Biological Inc), Mouse anti-human PD-1 antibody (ab52587, abcam), anti-human PD-1 antibody (130-096-166, Miltenyi Biotec), anti-human IgG-Fc-APC (409305, Biolegend), donkey anti-mouse IgG secondary antibodies (A10037, ThermoFisher), PLX302 vector (25896, addgene), VECTASHIELD mounting medium comprising DAP1 (H-1200, Vector laboratories), cell counting kit (CCK-8, DOJINDO), RPMI1640 (R6504, Sigma), bovine serum (SH30084, Hyclone), bovine serum albumin (V900933, Sigma), SDS(A600485, sangon).

Example 1. Screening and Synthesis of PD-1 Non-Antibody Binding Protein (PD-1-nABP), Which Mainly Includes Library Screening, ELISA Screening, and Sequencing Assay to Determine Sequences.

1) Screening of T7 phage library, was carried out according to an instruction of commercially available T7 phage library (T7 Selector Human Lung Tumor cDNA Library, D00154997, Novagenor), the instruction was shown as follows (screening diagram is seen from FIG. 1A):

1. PD-1 recombinant protein was coated on 96-well plates at 4° C. overnight;
2. The protein was washed three times with distilled water and then was blocked by using 5% skim milk powder at room temperature (hereinafter described as RT) for 1 hour:
3. T7 phage library was added to 5403 host bacteria (obtained by culturing and shaking in M9/LB medium, the same below), they were cultured at 37° C. for 4 hours, to obtain a lysate;
4. The lysate was centrifuged at 8000 g for 10 min to obtain a supernatant that is T7 phage library;
5. A titer determination was performed on the above obtained library to obtain the titer of the T7 phage library;
6. The volume of the T7 phage library for screening was calculated according to a formula "required volume for screening=$1.2 \times 10^7 \times$monoclonal repeat number (100)";
7. After 5% skim milk powder was mixed with T7 phage library at a ratio of 1:1, the mixture was added to the 96 well-plates coated with PD-1 recombinant protein, and placed at RT for 45 minutes;
8. The mixture was washed five times with 0.1% TBST;
9. 200 μl of 1% SDS was added to perform elution, RT×15 min;
10. After the cells were dissociated merely, the elutant was transferred to an EP tube;
11. 10 μl of eluant was taken to determine titer for calculating enrichment ratio;
12. 5 μl of round 1 eluant was taken and then added to a 2 ml of 5403 bacteria solution, followed by shaking the mixture at 37° C.×ON (overnight, the same below);
13. The mixture was centrifuged at 8000 g×10 min, and then supernatant was taken to obtain an amplified solution after round 1 screening;
14. 10 μl of the amplified solution was taken and added to the 5403 bacteria solution, then they were kept shaking at 37° C. for 3 hours;
15. The mixture was centrifuged at 8000 g×10 min, and then supernatant was taken to obtain a round 2 amplified solution (round 2 amplification) after the round 1 screening;
16. 10 μl of round 2 amplified solution after the round 1 screening was taken to perform a titer determination;
17. Based on calculated titer, the required volume for round 2 screening was calculated according to the above formula;
18. The steps in round 2, 3 and 4 screening were the same with round 1 (7-15), and a stock solution after the round 4 elution was obtained.

Result: phage having a titer of $5.4 \times 10^{10}$ cfu was used at first, and an obvious enrichment of the phage can be seen (FIG. 1C) after 4 rounds screenings (FIG. 1B). The enriched phage library was conserved for use.

(2) ELISA Screening 1. the stock solution after the round 4 elution was coated on a culture plate and cultured ON. Monoclonal plaque was picked and added to 5403 bacteria solution, cultured ON with shaking.
2. PD-1 recombinant protein was coated on 96-well plates, 4° C.×ON.
3. 1 ml of the bacteria solution was taken, and then it was centrifuged at 8000 g for 10 min, to obtain a supernatant which contains T7 phage.
4. 50 μl of 3% skim milk power was added to 100 Id of T7 phage and mixed well, then the mixture was added to the 96-well plate coated with PD-1 recombinant protein.
5. The plate was cultured at 37° C. for 1 hour.
6. After removing solution, the plate was washed 5 times with TBST.
7. The T7 phage antibody (T7 tail-fiber monoclonal antibody) was diluted at a ratio of 1 to 2500, then the diluent was added to the plate with 100 μl per hole, 4° C.×ON.
8. Primary antibody solution was removed and the plate was washed 5 times with TBST.
9. Secondary antibodies (goat anti-mouse IgG) being diluted at a ratio of 1:5000 was added, RT×1 hour.
10. The secondary antibody solution was removed and the plate was washed 5 times with TBST; TBST was added to the plate once again, and the plate was kept shaking for 10 min.
12. 100 μl of 250 mM HCl was added to terminate the reaction.
13. Absorbance values were detected at 450 nm by an enzyme-labeled instrument.
14. Samples which had high absorbance values were selected and cloned, then PCR detection and sequencing were performed subsequently. The inserted DNA fragments of each phage were analyzed through alignment with T7 phage by using a DNASTAR software, and were analyzed by BLAST on the NCBI website afterwards. The amino acid sequence of PD-1-nABP was determined finally, and peptides were synthesized artificially (CHINAPEPTIDES CO., LTD.). Fluorescent tag proteins such as FITC (green fluorescence) were added to the N-terminal of some PD-1-nABP as required, to prepare PD-1-nABP fluorescent reagent with purity of more than 95%.

Experimental results: three monoclonal phages with strong binding ability to PD-1 are picked out through detecting by ELISA, and named as nABP282, nABP283 and nABP284 (or PD-1-nABP282, PD-1-nABP283, PD-1-nABP284) respectively, and their detected absorbance values are shown in FIG. 1D.

The sequences of PD-1-nABP282, PD-1-nABP283, PD-1-nABP284 are shown in sequences 1-3 of a sequence listing accordingly.

Example 2. Construction of PD-1 Over Expressed Lentiviral Vector and Transfection and screening of PD-1 Over Expressed Cell Strains 1. Primer sequences corresponding to full length of CDS of PDCD1 gene was designed to synthesize the primers.
2. cDNA of PBMC was extracted to perform a PCR amplification of full length of PDCD1 gene by using the above primers.
3. After the product ran in gel, an obvious band at 867 bp could be observed. The gel was extracted (Acy Rep DNA extraction kit, the same below) for sequencing, and once the sequence was determined to be correct, the sequenced sequences were conserved.
4. The conserved DNA was linked to T vector and transformed. After the bacteria solution was coated on a plate and cultured overnight, the bacteria was taken to amplify with PCR. The amplified bacteria was checked whether it has a proper band position, after that, 10 positive cloning sequences were picked for sequencing. If the sequenced sequence was correct, the cloning sequences were conserved.
5. pENTRY vector and the conserved plasmid were digested by double enzymes (Not I enzyme and Sgs I enzyme), then product ran in gel, after photographing the gel to check whether a position of band that was correct, the gel was extracted;
6. The product extracted from the amplified plasmid was linked to pENTRY vector by T4 ligase, 16° C.×ON
7. The linked product was transformed, the bacteria solution was coated on a plate and cultured overnight. After that, the bacteria was taken to amplify with PCR, and the amplified bacteria was checked whether it has a proper band position. The cloning sequence was sent to perform sequencing, if the sequenced sequence was correct, the linked products (plasmid) were conserved;
8. LR recombinant reaction was performed by using PLX302 vector and the above linked product. The reaction product was transformed, and the bacteria solution was coated on a plate and cultured overnight. After that, some bacteria were taken to amplify with PCR, then it is checked whether a position of band that was correct. 5 positive cloning sequences were picked to perform sequencing, if the sequenced sequence was correct, the cloning sequences were conserved to obtain a PD-1 over-expressed lentiviral vector;
9. The PD-1 over-expressed lentiviral vector was packaged by 293T cells to obtain packaged lentiviral solution;
10. Jurkat cells (obtained from Shanghai cell bank of Chinese Academy of Science) were transfected by the packaged lentiviral solution;
11. Puromycin was used for screening, and stably expressed PD-1 cell strains were obtained, named as OE-Jurkat.

Figure 2A:
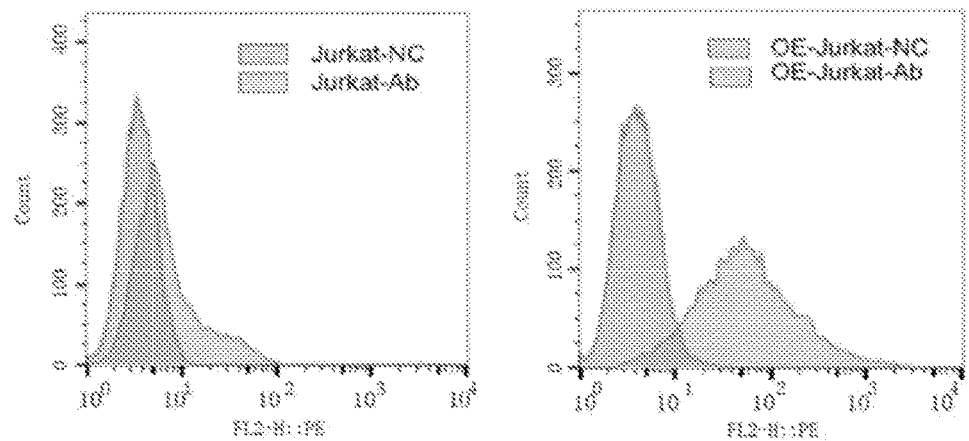
FIG. 2A depicts testing results of flow cytometry of PD-1 expression in OE-Jurkat cells and Jurkat cells.
Figure 2B:
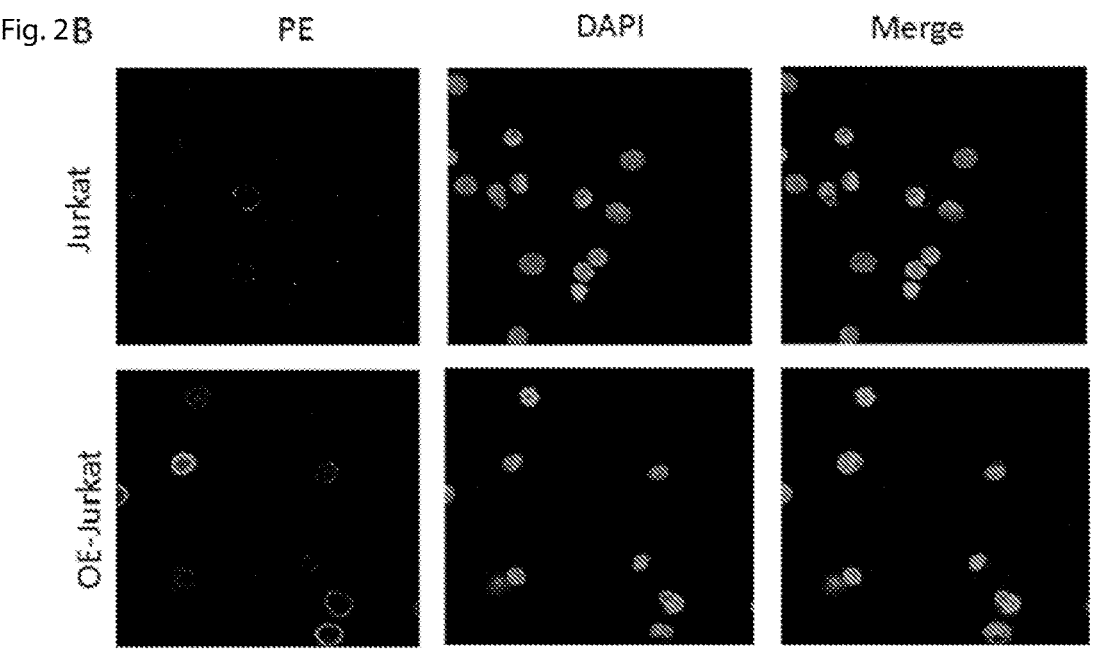
FIG. 2B depicts testing results of immunofluorescence co-labeling of fluorescent nABP284 and antibody in OE-Jurkat cells and Jurkat cells.

After construction of PLX302 lentiviral vector and transfection of Jurkat cells, stably expressed PD-1 cell strains are obtained and named as OE-Jurkat. The result analyzed by flow cytometry shows that there are 72% cells expressing PD-1 protein in OE-Jurkat cells and the expression of PD-1 of OE-Jurkat cells is significantly up-regulated (FIG. 2A); it is further proved by cell immunofluorescence that OE-Jurkat cells express PD-1 protein, and the PD-1 protein is expressed on cell membrane (FIG. 213).

Example 3. Verification of PD-1-nABP284 Binding to PD-1 Molecule (1). It was found that PD-1-nABP284 binds to PD-1 protein of total protein of OE-Jurkat cells through an immunoprecipitation assay.

The immunoprecipitation (IP) assay was carried out as following steps:

1. OE-Jurkat cells were collected, $4.5 \times 10^6$/group;
2. The cells were washed twice with PBS and then supernatant was removed completely to obtain cell precipitation;
3. The cells were resuspended in 500 µl of 1×Lysis buffer (total protease inhibitor PMSF added), and then were divided into two groups (an experimental group and a control group)
4. For each group, ultrasonication was performed 4 times to break the cells, and 4 s for each time. After that, the cells were placed on ice for 30 minutes
5. The cells were centrifuged at 10000 rpm for 10 min and the precipitation was removed to obtain a supernatant, i.e., total cell protein.
6. 10% goat serum was added and mixed well, and the mixture was placed on ice for 1 hour.
7. 100 µl of agarose magnetic beads (Millipore 16-266, being washed three times with 1× wash buffer, the same below) were added, 4° C.×1 h×shaking.
8. After centrifuging (14000 rpm×5 s, the same below), the magnetic beads were removed.
9. For the experimental group, 2 µl of PD-1 antibody (ab52587, 1 mg/ml, the same below) was added to the supernatant; for the control group, 2 µl of 1×wash buffer was added; 4° C.×ON×shaking for both groups.
10. For each group, 20 µl of the magnetic beads were added, 4° C.×1 h×shaking each.
11. After centrifugation, the supernatant was removed to obtain a precipitate, i.e., a complex of PD-1 protein—PD-1 antibody—magnetic bead.
12. The complex was resuspended in 500 µl of 1× wash buffer, after that, PD-1-nABP284 at a concentration of 15 µg/ml was added, 4° C.×2.5 h×shaking×being shielded from light.
13. After centrifugation, the supernatant was removed to obtain a precipitate, i.e., a complex of 284 nABP-PD-1 protein—PD-1 antibody—magnetic bead.
14. The complex was washed three times with 1× wash buffer, and supernatant was removed completely.
15. 20 µl of sample buffer was added and mixed well, 50° C.×10 min.
16. The magnetic beads were removed through centrifugation, and DTT was added to the supernatant until the final concentration reached 100 mM.
17. A fluorospectro photometer (NanoDrop 3300) was used for detecting.

Figure 3A:
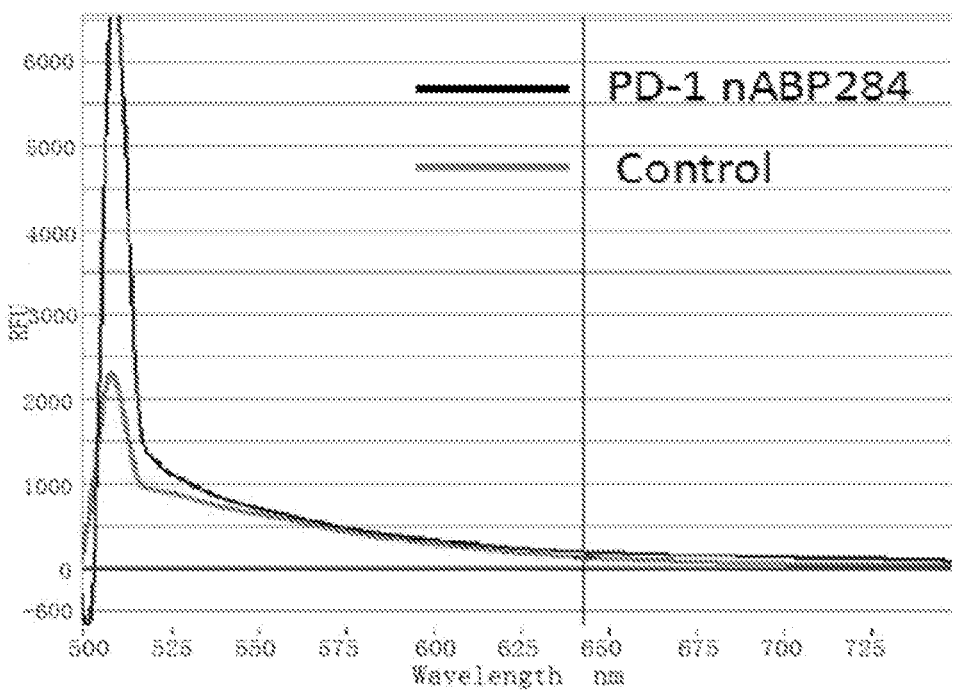
FIG. 3A depicts fluorescence results of immunoprecipitation assay after fluorescent nABP284 binds to total cellular proteins.

Through the IP assay, PD-1 protein of OE-Jurkat cells is precipitated by using PD-1 antibody, and then interacted with PD-1-nABP284. Micro-fluorescence of the reactant is detected by the fluorospectro photometer (FIG. 3A), it can be seen that fluorescence intensity indicated by the black curve for the experimental group is significantly stronger than that for the control group, proving that the protein precipitated by PD-1 antibody is able to bind to PD-1-nABP284.

(2). It was found that PD-1-nABP284 is capable of binding to PD-1 protein on the surface of cells by an immunofluorescence assay.

The immunofluorescence (IF) assay was carried out as following steps:

1. OE-Jurkat cells, PBMC and PD-1 cells in lymph gland were collected, 1×10$^6$ for each group, and then the cells were resuspended in 1 ml of PBS.
2. PD-1-nABP284, nABP282 and nABP283 at a concentration of 15 μg/ml was respectively added to these groups, RT×30 min.
3. For each group, the mixture was washed once with PBS (centrifuged at 1000 rpm for 5 min, the same below).
4. 4% PFA was used for fixation, RT×20 min.
5. PBS was used for one wash.
6. 10% goat serum is added to block the mixture, RT×1 h.
7. Centrifugation was performed to remove the supernatant completely
8. PD-1 primary antibody (ab52587, 1 mg/ml, the same below) was incubated; for the control group, 10% goat serum blocking reagent was added, both groups were cultured at 4° C. and shielded from light.
9. PBS was used for one wash.
10. Secondary antibodies (rabbit anti-mouse IgG 568) were incubated, RT×1 h.
11. PBS was used for one wash.
12. Anti-fade mounting medium was used for mounting.
13. A laser confocal microscopy was used for observing.

The IF results show that nABP284 is capable of binding to peripheral blood mononuclear cells (PBMC) and PD-1$^+$ cells of OE-Jurkat cells. As shown in FIG. 3C, PD-1 protein molecules on the surface of cells are labelled by red fluorescence, and PD-1-nABP284 is labelled by green fluorescence. Overlapping of two kinds of fluorescence can be observed in both primary cultured PMBC and OE-Jurkat cell strains, and this indicates the colocalization of PD-1-nABP284 and PD-1 on cells. In addition, tissue slice of lymph node was taken, through which the colocalization can also be observed (FIG. 3C). However, PD-1-nABP282 and PD-1-nABP283 are not capable of binding to PBMC and OE-Jurkat cells.

(3). It was found that the binding capability of PD-1-nABP284 to OE-Jurkat cells is higher through flow cytometry.

The flow cytometry experiment was carried out as following steps:

1. OE-Jurkat cells and Jurkat cells were collected and counted, 5×10$^5$ for each group, and the cells were resuspended in 1 ml of PBS.
2. nABP284 at a concentration of 15 μg/ml was added to each group, RT×10 min.
3. PBS was used for one wash (centrifuged at 1000 rpm for 5 min, the same below) and 100 μl of 0.5% BSA was used for resuspension.
4. 10 μl of primary antibody (ab52587) was added, 4° C.×10 min.
5. PBS was used for one wash.
6. 500 μl of PBS was used for resuspension, and then a flow cytometer was used for testing.

Figure 3B:
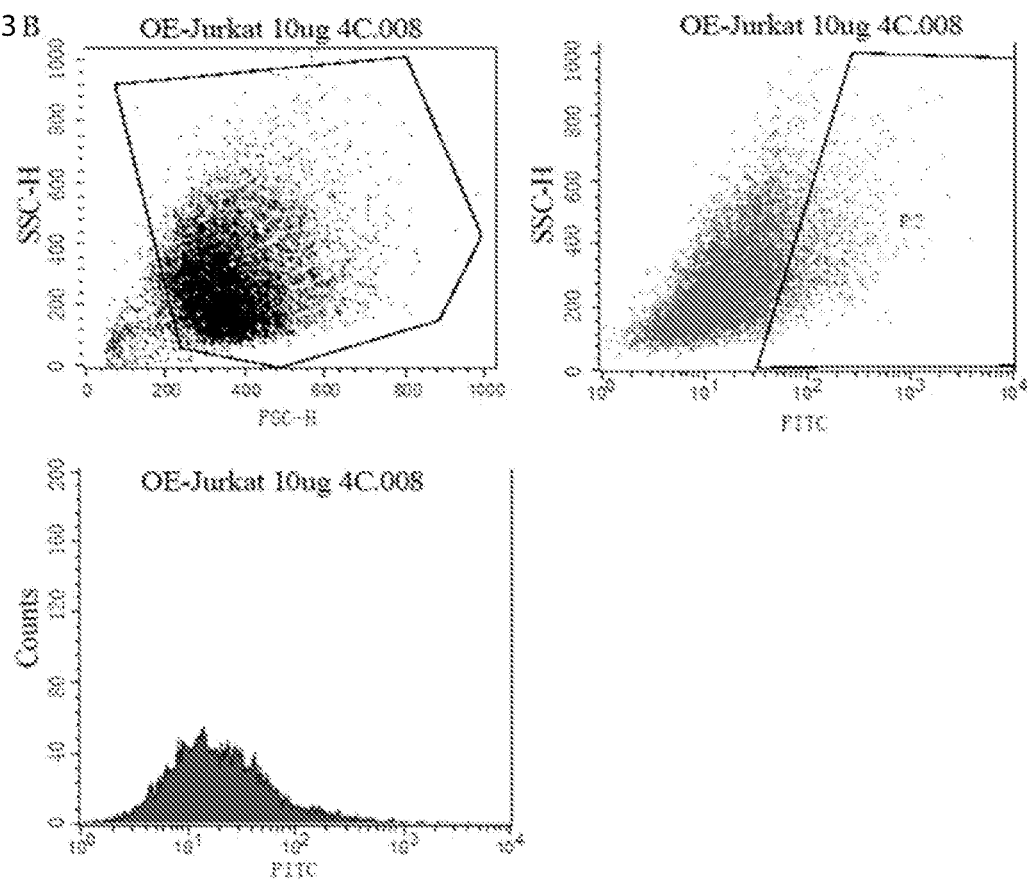
FIG. 3B shows testing results of binding effect of PD-1-nABP284 with OE-Jurkat and Jurkat cells, respectively.
Figure 3C:
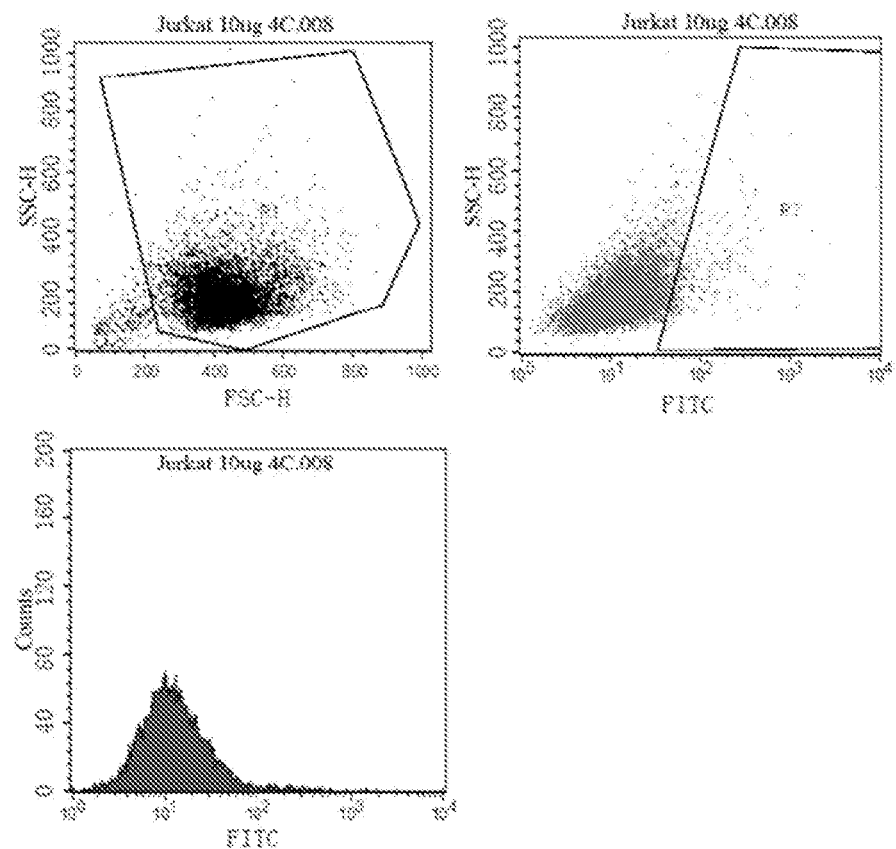
FIG. 3C depicts testing results of immunofluorescence assay of co-labeling the PD-1-nABP284 binding to PBMC, OE-Jurkat, and PD-1 positive cells in lymph node.
Figure 3C:
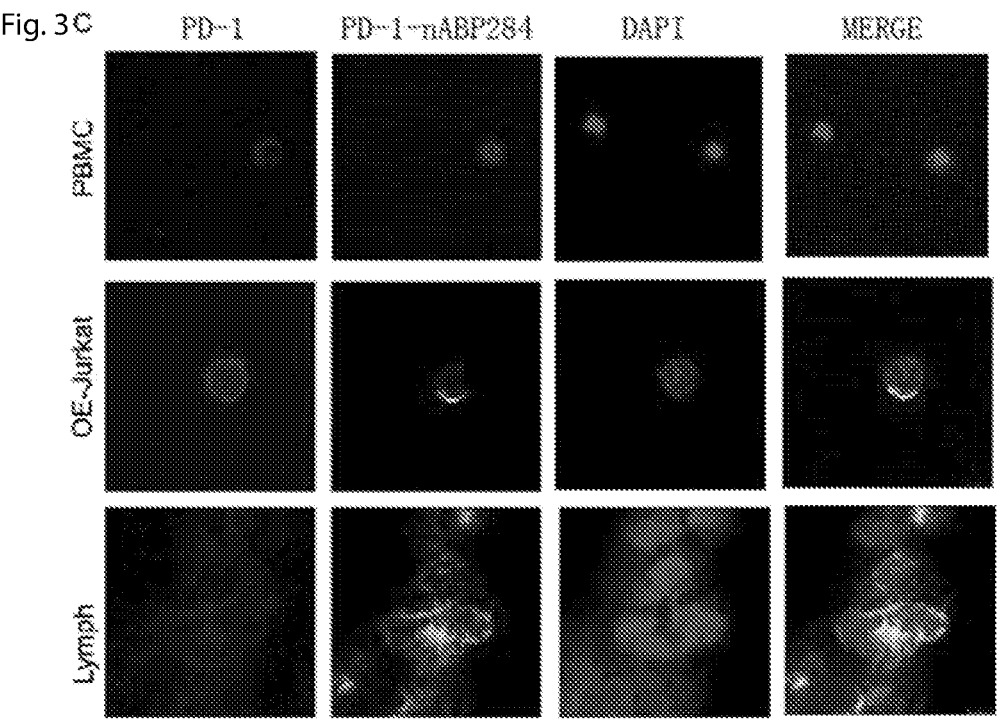

The result is shown in FIG. 3B. It can be found through the flow cytometry that the binding rate of PD-1-nABP284 to PD-1 over expressed OE-Jurkat cells is higher than that of Jurkat cells, indicating that PD-1-nABP284 is capable of binding to PD-1 protein on the surface of living cells.

Example 5. Comparison of Peptide Binding Capability and Comparison of Blocking effects on PD-1/PD-L1 Pathway (1) The peptide binding capability assay was carried out as following steps:

1. OE-Jurkat cells were collected and counted, 5×10 for each group, and then the cells were resuspended in 1 ml of PBS;
2. PD-1-nABP282, nABP283 and nABP284 at concentration of 15 μg/ml were respectively added these groups, RT×10 min;
3. Each group was washed once with PBS (centrifuged at 1000 rpm for 5 min, the same below) and then was resuspended in 100 μl of 0.5% BSA;
4. 10 μl of PD-1 antibody was added, 4° C.×10 min;
5. PBS was used for one wash;
6. Each group was resuspended in 500 μl of PBS, and the flow cytometry was used for detecting.

Figure 2C:
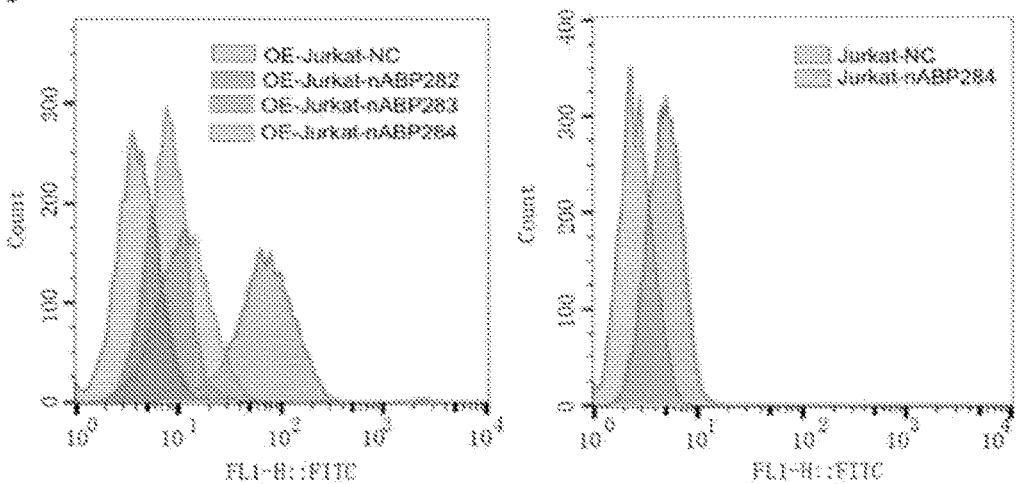
FIG. 2C depicts testing results of flow cytometry of affinity of nABP284, nABP283, nABP282 to PD-1 on the surface of OE-Jurkat cells.

The results are shown in FIG. 2C.

(2). Detection of blocking for PD-1/PD-L1 binding

1. OE-Jurkat cells were collected and counted, 5×1 for each group, and then the cells were resuspended in 1 ml of PBS;
2. nABP282, nABP283 and nABP284 at a concentration of 15 μg/ml were respectively added to these groups, RT×10 min;
3. Each group was washed once with PBS (centrifuged at 1000 rpm for 5 min, the same below) and then was resuspended in 100 μl of 0.5% BSA;
4. For the experimental group, 10 μl of PD-L1-Fc protein (0.25 mg/ml) was added, RT×20 min;
5. PBS was used for two washes, and anti-human IgG-Fc-APC was used for staining at 4° C. for 20 minutes;
6. The stained cell was washed once and then was resuspended in 500 μl of PBS, the flow cytometry was used for detecting.

The above operations were applied for the experimental group; while for the negative control group, anti-human IgG-Fc-APC was added, and it just need washing once; for a positive control group, the operations were almost the same as the experimental group except without addition of nABPs.

It is shown by flow cytometry analysis that after being incubated with OE-Jurkat cells, nABP284 shows high affinity to OE-Jurkat cells, while nABP282 and nABP283 both show lower affinity (FIG. 2C). The result of IF is conformity with the result of flow cytometry (FIG. 2D).

When double staining was carried out for nABP284 and anti-human PD-1 antibody, PE (PD-1) and FITC (nABP) signals can be detected on the cell membrane of OE-Jurkat cells. However, when double staining was carried out for nABP282 and 283, only PE signal of PD-1 antibody is detected. These show that nABP284 has a higher affinity to PD-1 receptor compared to other two nABPs.

Figure 4:
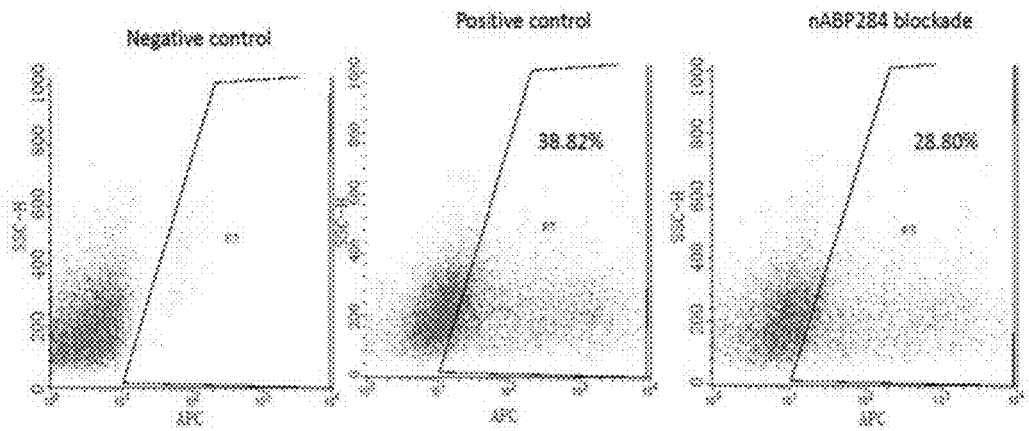
FIG. 4 depicts testing results of an experiment in which PD-1-nABP284 blocks PD-1/PD-L1 binding.

As shown in FIG. 4, when nABP284 is added, the percentage of cells stained with anti-human IgG-Fc-APC decreases and is lower than that of the positive control group, indicating that nABP284 weaken PD-L1-Fc protein binding to PD-1. The result shows that nABP284 is capable of blocking the PD-1/PD-L1 pathway.

Example 6. Testing Results of Enhancement of the Secretion of Interleukin-2 Due to PD-1-nABP284 Blocking PD-1/PD-L1 Binding 1. The expression of PD-1 of CAL27 tongue squamous cell carcinoma cell strains was detected according to the above flow cytometry assay method, and the results were shown in FIG. 5 that all CAL27 cells expressed PD-L1.

2. The CAL27 tongue squamous cell carcinoma cell strains and OE-Jurkat cells were taken in equal amount and co-cultured in a culture dish, afterwards PD-1-nABP282, nABP283 and nABP284 at a concentration of 15 µg/ml were added respectively, while an equal amount of PBS was added for the control group.

3. After being co-cultured for 24 hours, the supernatant was collected, and then a human interleukin-2 ELISA kit (ab46054) was used for detecting the secretion level of interleukin-2 in each group.

Figure 5:
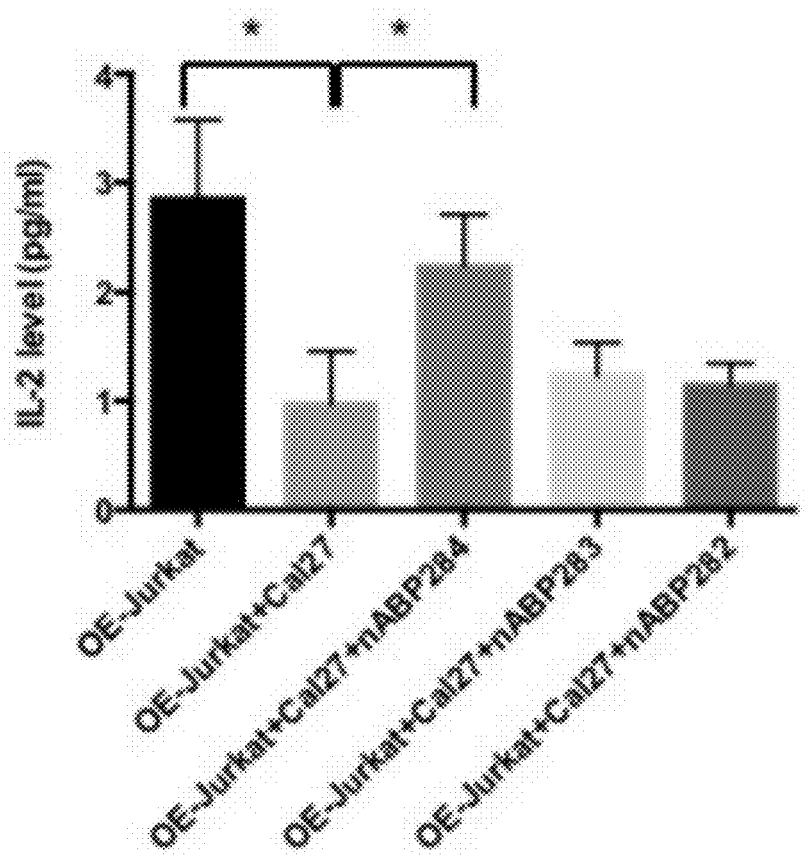
FIG. 5 depicts testing results of enhancement of secretion of cellular interleukin due to PD-1-nABP284 blocking the PD-1/PD-L1 binding.

As shown in FIG. 5, after the OE-Jurkat cells and CAL27 tongue squamous cell carcinoma cell strains are co-cultured, the amount of interleukin-2 in the supernatant significantly decreases. For the experimental group with nABP284 addition, the inhibition of interleukin-2 secretion caused by co-culturing is relieved. This indicates that PD-L1 secreted by CAL27 tongue squamous cell carcinoma binds to PD-1, which inhibits the expression of interleukin-2, while nABP284 has a competition with PD-L1 to bind to PD-1, which relieves inhibiting effect of PD-L1. Moreover, after the control group containing nABP282 or nABP283 without specifically binding to PD-1 is added to the culture medium, no obvious impact on the secretion of interleukin-2 in the condition of co-culturing, indicating that nABP284 blocks PD-1/PD-L1 pathway and specifically relieves inhibition of humoral immunity caused by the pathway.

Example 7. Testing Results of Enhancement of Tumor Killing Effect on Lymphocytes Tumor Due to PD-1-nABP284 Blocking the PD-1/PD-L1 Binding 1. Peripheral blood mononuclear cells were isolated by using gradient centrifugation, and according to a cultural method of improving cytokine-induced killer cell (iCIK), OKT3 monoclonal antibody (Janssen Pharmaceutical, Japan), 1000 U/ml of rhIFN-γ (Clongamma, Shanghai, China), and 500 U/ml of rhIL-2 (Slpharm, Beijing, China) were added to stimulate T cells to amplify for 24 hours, culture solution containing 500 U/ml of rhIL-2 was replaced every three days. After being cultured for 10-14 days, cells were collected and used for a tumor killing experiment.

2. iCIK cells and CAL27 tongue carcinoma cells were co-cultured at a ratio of 0.16, 0.31, 0.62, 1.25, 2.5, 5 and 10 to 1 respectively, wherein PD-1-Nabp284 was added for the experimental group and an equal amount of PBS was added for the control group.

3. After being cultured for 24 hours, a CytoTox96® non-radioactive cytotoxicity kit (Promega, USA) was used for detecting the activity of cellular lactate dehydrogenase (LDH), and absorbance at wavelength 490 nm was determined to calculate the tumor killing effect of lymphocytes.

Figure 6:
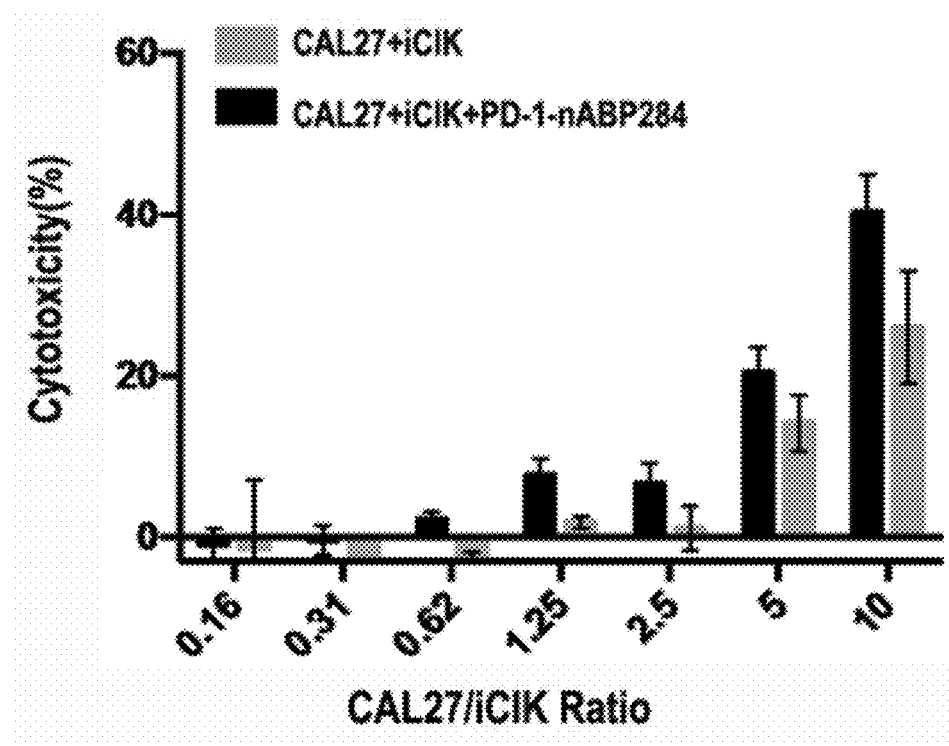
FIG. 6 depicts testing results of enhancement of the lymphocytes tumor-killing ability due to PD-1-nABP284 blocking the PD-1/PD-L1 binding.

As shown in FIG. 6, after iCIK cells and CAL27 tongue carcinoma cells are co-cultured for 24 hours, the tumor killing effect of the experimental group with nABP284 is higher than that of the control group, and the biggest difference appears at a ratio of 10 to 1. This indicates that PD-L1 secreted by CAL27 tongue carcinoma cells binds to PD-1, which may inhibit cellular immune response, and nABP284 has a competition with PD-L1 to bind to PD-1, which relieves the immunosuppressive effect on tumor cells and enhances the tumor killing effect of iCIK cells.

Example 8. Effect of PD-1-nABP284 on Proliferation of OE-Jurkat Cells and Toxicity of PD-1-nABP284 to OE-Jurkat Cells The experiment of effect of PD-1-nABP284 on cell proliferation was carried out as following steps:

1. OE-Jurkat cells were collected and counted, and then were diluted with basal culture medium (RPMI1640 culture medium) until the cell amount reached $1 \times 10^5$/ml;

2. 1 ml of the diluent obtained from the above step 1 was added to a 24-well plate 3. 5 µg/ml of 284nABP was added for the experimental group, while basal culture medium in a corresponding amount was added for the control group;

4. Cell counting (3 duplications) was performed every day for a total of five days;

5. The cell counting data was obtained and statistically analyzed.

The cytotoxicity experiment of PD-1-nABP284 was carried out as following steps:

1. OE-Jurkat cells were collected and counted, and then were diluted with basal culture medium (RPMI1640 culture medium) until the cell amount reached $1 \times 10^6$/ml;

2. The cell diluent obtained from the above step 1 was added to a 96-well plate;

3. A corresponding amount of nABP284 was added to obtain a concentration gradient of 0, 2, 5, 10, 50 and 100 µg/ml respectively, and then mixed well (3 duplications for each concentration gradient)

4. After the cells were cultured for 24 H and 48 H respectively, cytotoxicity detection reagent CCK-8 was added in 10 µl/hole, and then was mixed well;

5. The cell was incubated at 37° C. for 1 h and it was found that the culture medium became yellow;

6. An enzyme-labeled instrument was used for detecting absorbance values;

7. The values were statistically analyzed.

Figure 7:
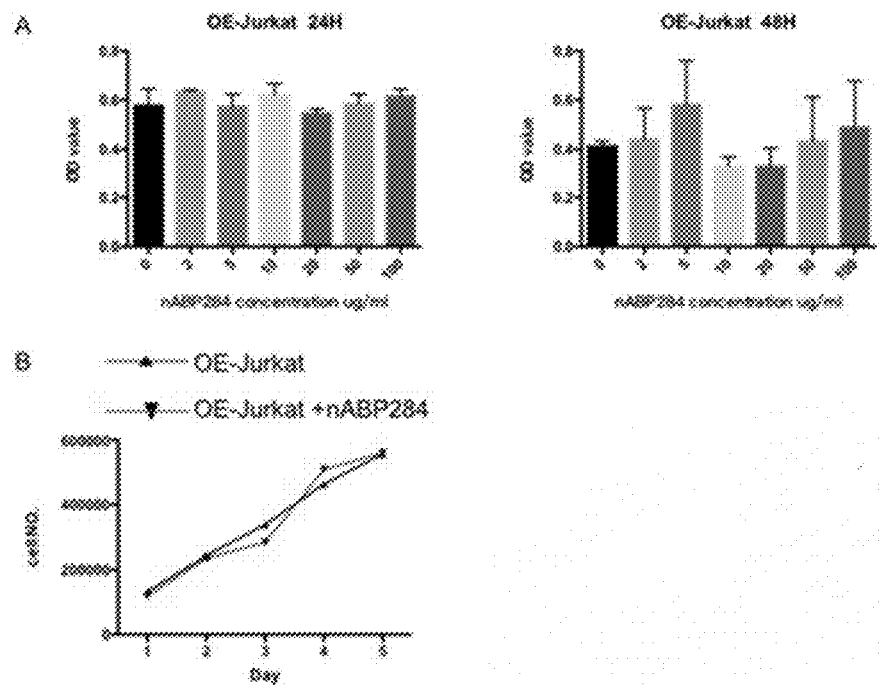
FIG. 7A depicts testing results of a cytotoxicity test of PD-1-nABP284.
FIG. 7B depicts testing results of effects of PD-1-nABP284 on cell proliferation.

The experimental result is shown in FIG. 7. The cytotoxicity of nABP284 to OE-Jurkat is measured by Cell Counting Kit-8 (CCK-8). As shown in FIG. 7A, after different concentrations (0-100 µg/ml) of PD-1-nABP284 were added and cultured for 24 h and 48 h, the activity of OE-Jurkat cells is not affected. FIG. 7B shows that after OE-Jurkat cells are cultured for 5 days in a culture medium with low level of serum and PD-1-nABP284 addition, no significant difference in cell proliferation rate between the experimental group and the control group is observed, indicating that PD-1-nABP284 binding to PD-1 does not affect the proliferation of OE-Jurkat cells.

Example 9. Metabolism of PD-1-nABP284 in Mouse

1. After an ethics application of animal experiment, one nude mouse was purchased from the Animal Experimental Center of Sun Yat-sen University.

2. nABP284 was diluted to 250 µl in a concentration of 4 mg/ml, with aseptic grade III water.

3. 250 µl of nABP284 was intravenously injected in the mouse tail.

4. The mouse was imaged in vivo imaging equipment, the equipment was set to image one picture every 3 minutes, for a total of 1 h, and a positive control hole (with a concentration of 0.4 mg/ml) was set.

Figure 8:
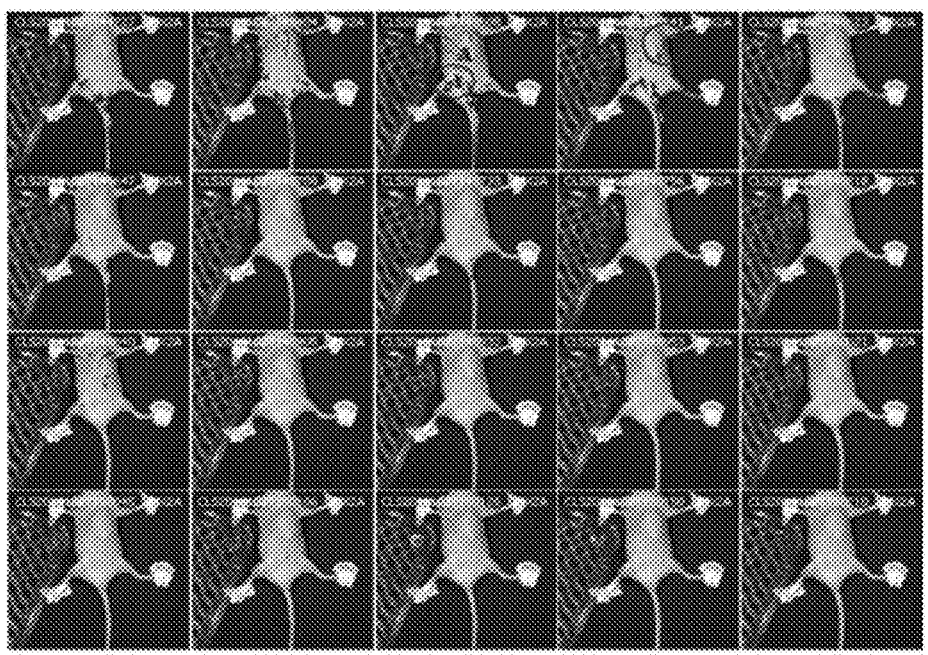
FIG. 8 depicts fluorescence images of metabolism of PD-1-nABP284 in mouse.

5. Imaging data was obtained and an analytical software was used for spectral separation to obtain localization and metabolic images of nABP284 fluorescence in mouse without FITC spectral interference Living mouse image is shown in FIG. 8. 1 mg of PD-1-nABP284 with FITC fluorescent label was intravenously injected into the mouse through the tail vein, and it was rapidly distributed through the blood circulation to the whole body. After 30 minutes, it can be seen that the PD-1-nABP284 was accumulated in inguinal lymph and axillary lymph of the mouse, and after 60 minutes of systemic metabolism, green fluorescence cannot be detected, indicating that PD-1-nABP284 injected into the mouse is substantially completely metabolized after 60 minutes. After injection of high concentration of PD-1-nABP284 with FITC fluorescence label, the mouse has stable vital signs, indicating that it is nontoxic to mouse.

The above are only examples of the present disclosure, and they are not intended to limit the present disclosure in any way. Any simple amendments, equivalent changes and modifications made in the above examples according to the technical essence of the present without departing from the contents of the technical solution of the present disclosure, are within the scope of technical solution of the present disclosure.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A non-antibody binding protein binding to a PD-1 receptor, wherein the non-antibody binding protein comprises SEQ ID NO: 1.

2. A method of blocking PD-1 pathway, comprising applying a non-antibody binding protein binding to a PD-1 receptor, wherein the non-antibody binding protein comprises SEQ ID NO: 1.

* * * * *

```
                          SEQUENCE LISTING

<160> NUMBER OF SEQ ID NOS: 3

<210> SEQ ID NO 1
<211> LENGTH: 37
<212> TYPE: PRT
<213> ORGANISM: Artificial sequence
<220> FEATURE:
<223> OTHER INFORMATION: PD-1-nABP284

<400> SEQUENCE: 1

Ser Arg Leu Lys Glu Ile Ala Asn Ser Pro Thr Gln Phe Trp Arg Met
1               5                   10                  15

Val Ala Arg Asn Thr Leu Gly Asn Gly Ala Lys Gln Ser Leu Asn Ile
            20                  25                  30

Glu His Ala Arg Leu
        35

<210> SEQ ID NO 2
<211> LENGTH: 11
<212> TYPE: PRT
<213> ORGANISM: Artificial sequence
<220> FEATURE:
<223> OTHER INFORMATION: PD-1-nABP282

<400> SEQUENCE: 2

Ser Ser Val Val Glu Ser Gly Trp Gly Gln Leu
1               5                   10

<210> SEQ ID NO 3
<211> LENGTH: 14
<212> TYPE: PRT
<213> ORGANISM: Artificial sequence
<220> FEATURE:
<223> OTHER INFORMATION: PD-1-nABP283

<400> SEQUENCE: 3

Ser Ser Arg Pro Arg Ser Leu Pro Gly His Gln Glu Ala Ser
1               5                   10
```